United States Patent [19]

Ramamurthy et al.

[11] Patent Number: 6,114,316
[45] Date of Patent: Sep. 5, 2000

[54] COMBINATION OF BISPHOSPHONATE AND TETRACYCLINE

[75] Inventors: Nungavarm S. Ramamurthy; Lorne M. Golub, both of Smithtown, N.Y.; Timo A. Sorsa; Olli P. Teronen, both of Helsinki, Finland; Tuula A. Salo, Oulu, Finland

[73] Assignee: Research Foundation of S.U.N.Y., Albany, N.Y.

[21] Appl. No.: 09/388,762

[22] Filed: Sep. 2, 1999

Related U.S. Application Data

[62] Division of application No. 09/161,804, Sep. 28, 1998.

[51] Int. Cl.$^7$ ............................ A61K 31/66; A61K 31/65
[52] U.S. Cl. ....................... 514/108; 514/102; 514/103; 514/104; 514/107; 514/152; 514/154
[58] Field of Search ................................. 514/102, 103, 514/104, 107, 108, 152, 154

[56] References Cited

U.S. PATENT DOCUMENTS

| | | | |
|---|---|---|---|
| Re. 34,656 | 7/1994 | Goulb et al. | 514/152 |
| 4,666,897 | 5/1987 | Golub et al. | 514/152 |
| 4,704,383 | 11/1987 | McNamara et al. | 514/152 |
| 4,935,412 | 6/1990 | McNamara et al. | 514/152 |
| 5,258,371 | 11/1993 | Golub et al. | 514/152 |
| 5,308,839 | 5/1994 | Golub et al. | 514/152 |
| 5,321,017 | 6/1994 | Golub et al. | 514/152 |
| 5,403,829 | 4/1995 | Lehitinan et al. | 514/102 |
| 5,442,101 | 8/1995 | Hanhijarvi et al. | 562/10 |
| 5,459,135 | 10/1995 | Golub et al. | 514/152 |
| 5,652,227 | 7/1997 | Pekka et al. | 514/75 |
| 5,668,120 | 9/1997 | Shinoda et al. | 514/102 |
| 5,773,430 | 6/1998 | Simon et al. | 514/152 |
| 5,880,111 | 3/1999 | Farcasiu et al. | 514/79 |

OTHER PUBLICATIONS

Ryan, M.E. et al., "Potential of Tetracycline to Modify Cartilage Breakdown in Osteoarthritis ", *Curr. Opin. Rheumatology,*8 (1996) 238–247.

Llano, E. et al., "Identification and Structural and Functional Characterization of Human Enamelysin (MMP–20), " *Biochemistry,*36 (1997) 15101–15108.

Salo, T. et al., "Enamelysin (MMP–20) is Expressed in Oral Squamous Cell Carcinoma Cells", *J. Dent. Res.,* 77 (1998) 829 Abstract No. 1978.

Birkedal–Hansen, H., "Proteclytic Remodeling of Extracellular Matrix", *Curr. Opin. Cell Biol.,*7 (1995) 728–735.

Woessner Jr., J. F., "Matrix Metalloproteinases and their Inhibitors in Connective Tissue Remodeling", *FASEB J.,* 5 (1991) 2145–2154.

Chandler, S. et al., "Matrix Metalloproteinases, Tumor Necrosis Factor and Multiple Sclerosis: An Overview", *J. Neuroimmunology,*72 (1997) 155–161.

van Hujsduijnen, R.H., "ADAM 20 and 21 ; Two Novel Human Testis–Specific membrance Metalloproteases with Similarity to Fertilin–α", *Gene,*206 (1998) 273–282.

Huovila, A.J. et al., "ADAMs and Cell Fusion", *Curr. Opin. Cell. Biol.,*8 (1996) 692–699.

Yagami–Hiromasa T. et al., "A Metalloprotease–Disintegrin Participating in Myoblast Fusion", *Nature,* 377 (1995) 652–656.

Perry, A.C. et al., Abstract: "Genetic Evidence for an Additional Member of the Metalloprotease–Like, Disintegrin–Like Cysteine–Rich (MDC) Family of mammalian Proteins and its Abundant Expression in the Testis", *Biochem. Biophys, Acta*(1994) 1207, 134–137.

Wolfsberg, T.G. et al., "ADAM, A Widely Distributed and developmentally Regulated Gene Family Encoding Membrance Proteins with a Disintegrin and Metalloprotease Domain", *Developmental Biology,*169 (1995) 378–383.

Watanabe, N. et al., "Processing and Release of Tumor Necrosis Factor α", *Eur. J. Biochem.,*253 (1998) 576–582.

Shapira, L. et al., "Tetracycline Inhbitors Porphyromonas Gingivalis Lipopolysaccharide–Induced Lesions in vivo and TNFαProcessing *in vitro,*" *J. Period. Res.,* 32 (1997) 183–188.

Sorsa, L. et al., "Idenification of Proteases from Periodontopathogenic Bacteria as Activators of Latent Human Neutrophil and Fibroblast Type Interstital Collagenases", *Infect. Immun.,*60 (1992) 4491–4495.

Sorsa, T. et al., "Activation of Type IV Procollagenase by Human Tumor Asociated Trypsin 2, " *J. Biol. Chem.,*272 (1997) 21067–21074.

Lowe, F.C. et al., Abstract: "Biochemical Methods for Predicting Metastatic Ability of Prostatic Cancer Utilizing the Dunning R–3327 Rat Prostatic Adenocarcinoma System As A Model ", *Cancer Res.,*44 (1984) 744–752.

Stetler–Stevenson, W.G. et al., "Tumor Cell Interactions with the Extracelluar Matrix During Invasion and Matastasis", *Annu. Rev. Cell Biol.,*9 (1993) 541–573.

Tryggvason, K. et al., "Proteolytic Degradation of Extracellular Matrix in Tumor Invasion", *Biochimica et Biophysica Acta,*907 (1987), 191–217.

Grenwald, R.A. et al., "In Vivo Sensitivity of the Three Mammalian Collagenases to Tetracycline Inhibition: Relationship to Bone and Cartilage Degradation", *Bone,*22 (1998) 33–38.

Bourguignon, L. et al., "CD–44V3–Cytoskeleton Interaction and Matrix Metalloproteinase (MMP–9) Association Promote Lymphocyte Infiltration into Pancreatic Islets in NOD Mice", *Mol. Biol. Cell,*8i Suppl (1997), Abstract No. 1603.

Liedtke, W. et al., "Effective Treatment of Models of Multiple Sclerosis by Matrix Metalloproteinase Inhibitors", *Annals of neurology,* 44 (1998) 35–46.

Li, H. et al., "Immunological Characterization of Cell–Syrface and Soluble Forms of Membrance Type 1 Matrix Metalloproteinase in Human Breast Cancer Cells and in Fibroblasts", *Mol. Carcinogensis,*22 (1998) 84–94, Abstr..

(List continued on next page.)

*Primary Examiner*—Frederick Krass
*Attorney, Agent, or Firm*—Hoffman & Baron, LLP

[57] ABSTRACT

Tissue-destructive conditions related to excess protemase activity in a biological system are treated or prevented by administering to the system a composition which combines a tetracycline and a bisphosphonate in synergistic proteinase inhibiting amounts.

8 Claims, 8 Drawing Sheets

OTHER PUBLICATIONS

Mallya, S.K. et al., "Intetaction of Matrix Metalloproteinase with Serine Protease Inhibitors", *Ann. NY Acad. Sci.,* 732 (1994) 303–314.

Zernicke, R.F. et al., "Administration of System Matrix Metalloproteinase Inhibitors Maintains Bone Mechanical Integrity in Adjuvant Arthritis", *J. Rheumatology,* 24 (1997) 1324–1331.

Sorsa, T. et al., "Functional Sites of Chemically Modified Tetracyclines: Inhibition of the Oxidative Activation of Human Neutrophil and Chicken Osteroclast ProMatrix Metalloptoteinase", *J. Rheumatology,* 25 (1998) 975–982.

Golub, L.M. et al., "Tetracyclines Inhibit Connective Tissue Breakdown by Multiple Non Antimicrobial Mechanisms", *Adv. Dental Research,* (1998) in press.

Mitscher L.A., *The Chemistry of the tetracycline Antibiotics,* Marcel Dekker, New York (1978), ch. 6, 165–218.

Giannelli, G. et al. "Induction of Cell Migration by Matrix Metalloproteinase–2 Cleavage of Laminin–5", *Science,* 277 (1997) 225–8.

Fleisch, H., "Biophosphonates: Mechanisms of Action", *Endocrine Reviews,* 19 (1998) 80.

Ramamurthy, N.S. et al., "The Effects of Alloxan Diabetics on Prolyl and Lysyl Hydroxylase Activity in Uminflamed and Inflamed Rat Gingiva", *Archs. oral Biol.,* 30 (1985) 679–683.

Hanahan, D. et al., "Pattern and Emerging Mechanisms of the Angiogenic Switch during Tumorigenesis", *Cell* 86 (1996) 353–364.

Teronen, O. et al., "Human Neutrophil Collagenase MMP–8 In Peri–Implant Sulcus Fluid and its Inhibition by Clondronate", *J. Dental Res.,* 76 (1997) 1529–1537.

Sorsa, T. et al., "Effects of Tetracycline on Neutrophil, Gingival, and Salivary Collagenase", *Ann. NY Acad. Sci.,* 732 (1994) 112–131.

Golub, L.M. et al., "A Matrix Metalloproteinase Inhibitor Reduces Bone–Type Collagen Degration Fragments and Specific Collagenases in Gingival Crevicular Fluid During Adult Periodontitis", *Inflamm. Res.,* 46 (1997) 310–319.

COMBINATION OF BISPHOSPHONATE AND TETRACYCLINE

CROSS REFERENCE TO RELATED APPLICATIONS

This application is a Divisional Application of co-pending U.S. application Ser. No. 09/161,804, filed on Sep. 28, 1998.

This invention was made with government support under R37DE03987 awarded by the National Institute of Dental Research (NIH). The government has certain rights in the invention.

The invention relates to a combination of tetracyclines and bisphosphonates which act synergistically to inhibit, reduce, down-regulate and/or prevent degradation of connective tissue, basement membrane as well as other factors in subjects susceptible to this type of tissue degradation.

BACKGROUND OF TEE INVENTION

Proteolytic activity is responsible for damage to connective tissues and basement membranes as a complication of the inflammatory and/or immune response and other disease processes, such as cancer cell invasion and metastasis. The inflammatory response contributes, for example, to the pathological changes in a number of acute and chronic processes involving diverse organs and tissues such as the lungs, bone, heart, joints, skin and periodontium, etc.

The proteinases involved in these responses or disease processes include matrix metalloproteinase (MMP's), MMP-like proteinases and related proteinases, serine proteinases and other proteinases. The MMP's are zinc and calcium-dependent for hydrolytic cleavage of substrate proteins and are secreted or released by a variety of host cells (e.g., polymorphonuclear neutrophils (PMN's), macrophages, bone cells, epithelium and fibroblasts). Certain other genetically distinct MMP's called membrane-type MMP's (MT-MMP's) are cell membrane-bound; others are secreted into the extracellular matrix (ECM). With serine proteinases, the amino acid serine acts as a nucleophile for hydrolytic cleavage of substrate protein. Serine proteinases are released, e.g., by triggered leukocytes, more specifically by the azurophilic granules of PMN's, and other cells including malignant tumor cells.

Several studies have shown that the expression and activities of MMPs are pathologically elevated over the body's endogenous anti-proteinase shield in a variety of diseases such as cancer metastasis, rheumatoid arthritis, multiple sclerosis, periodontitis, osteoporosis, osteosarcoma, osteomyelitis, bronchiectasis, chronic pulmonary obstructive disease, skin and eye diseases. Proteolytic enzymes, especially MMPs, are believed to contribute to the tissue destruction damage associated with these diseases.

Some metalloproteinases (MMP's) and their association with diseases are discussed by M. E. Ryan, et al., *Curr. Op. Rheum.,* 1996, 8:238–247. More than twenty MMP's have been identified and the number is growing. These include Interstitial Collagenases MMP-1 (fibroblast-type), MMP-8 (polymorphonuclear leukocyte-PMNL-type or collagenase-2), MMP-13 (collagenase-3); Gelatinases MMP-2 (72-kD gelatinase A) and MMP-9 (92-kD gelatinase B); Stromelysins MMP-3 (stromelysin-1), MMP-10 (stromelysin-2), and MMP-7 (matrilysin or putative metalloproteinase (PUMP)-1); Membrane Type (MT-MMP's), MMP-14 ($MT_1$-MMP), MMP-15 ($MT_2$-MMP), MMP-16 ($MT_3$-MMP); others are, for example, MMP-11 (stromelysin-3), MMP-12 (macrophage metalloelastase) and MMP-20. Enamelysin (MMP-20) is described by Llano et al., *Biochem.* 1997, 36:15101–15108, and can also be expressed by human cancer cells such as squamous carcinoma cells of the human tongue indicating its potential contribution to cancer progression and invasion (Salo et al., *J. Dent. Res.* 1998, 77:829, Abstr. No. 1978). Related proteinases include TACE's and ADAM's fertilin or meltrin (metalloproteinase/disintegrin).

MMP's, MMP-like and related proteinases such as TACE's, ADAM's, etc., are involved in processing and modification of molecular phenomena such as tissue remodeling (Birkedal-Hansen, *Current Opin. Cell Biol.* 1995, 7:728–735; J. F. Woessner, Jr., *FASEB J.* 1991, 5:2145–2154, cytokine actions (S. Chandler et al., *J. Neuroimmunol.* 1997, 72:155–161), cell-cell fusion (R H van Huijsduijen. *Gene* 1998, 206:273–282; Huovila et al., *Curr. Opin. Cell Biol.* 1996, 8:692–699; Yagami-Hiromasa et al., *Nature* 1995, 377:662–656), angiogenesis, growth factor actions, integrin and other adhesion factors and their receptor processings. See also, A. C. Perry et al., *Biochem. Biophys Acta* 1994, 1207:134–137. The ADAM enzymes are membrane proteins with A Disintegrin and Metalloproteinase Domain (Wolfsberg et al., *Dev. Biol.* 1995, 169:378–383). TACE is tumor necrosis factor converting enzyme.

MMP-like proteinases and related proteinases are metalloproteinases distinct from classic MMP's and can be involved in cellular processing of pro-TNF alpha (Tumor Necrosis Factor), cellular shedding of cytokine receptors, adhesion molecules, etc. as described by S. Chandler et al., *J Neuroimmunol.* 1997, 72:155–161. MMP's and MMP-like and related enzymes, e.g., ADAM's, TACE's, etc., also mediate the release of TNF alpha (Watanabe et al., *Eur. J. Biochem.* 1998, 253:576–582) and are involved in membrane-bound processing of TNF alpha by monocytes induced by bacterial-virulence factors. This event is mediated by membrane-bound metalloproteinases. Shapira et al., *J. Period. Res.* 1997, 32:183–185.

There is extensive evidence for the association between proteinases and a large number of disease processes. Microbial proteinases can act in concert with host proteinases in the promotion of tissue destruction as seen in periodontium (Sorsa et al., *Infect. Immun.* 1992, 60:4491–4495). Recent studies indicate that a serine protease, i.e., elastase, may play a role in connective tissue breakdown and tissue invasion in the Dunning rat model of cancer invasion and metastases (prostate cancer) (Lowe and Isaacs, *Cancer Res.* 1984, 44:744–52). Also involved in initiating the proteinase cascade that mediates tumor invasion and metastasis are trypsin and chymotrypsin-like activity (Sorsa et al., *J. Biol. Chem.* 1997, 272:21067–21074). Serine proteinase is expressed in human cancers such as ovarian carcinoma and cholangiosarcoma (Sorsa et al., *J. Biol. Chem.* 1997, 272:21067–21074).

The role of MMP's has been well-established in a great many disease states, e.g., tumor invasion and metastasis (Stetler-Stevenson et al., *Annu. Rev. Cell Biol.* 1993, 9:541–73; Tryggvason et al., *Biochim. Biophys. Acta* 1987, 907:191–217) and bone and cartilage degradation (Greenwald et al., *Bone* 1998, 22:33–38; Ryan et al., *Curr. Op. Rheumatol.* 1996, 8;238–247). MMP-20 is expressed by oral squamous cell carcinoma cells (Salo et al., *J. Dent. Res.* 1998, 77:829, Abstr. No. 1978). Bourguignon et al. (*Mol. Biol Cell.* 1997, 8i Supplement, Abstract 1603) describe the association of metalloproteinase with matrix degradation as being responsible for promoting lymphocyte infiltration that destroys insulin-producing pancreatic islet cells. Cytokines (TNF alpha) and MMP's have also been implicated in the pathogenesis of multiple sclerosis (Liedtke et al., *Ann. Neurol.* 1998, 44:35–46; Chandler et al., *J Neuroimmunol.* 1997, 72:155–71). MT$_1$-MMP has been found to act in the growth and spread of breast cancer cells (Li et al., *Mol. Carcinog.* 1998, 22:84–89).

There are many other disorders in which extracellular protein degradation/destruction plays a prominent role. Examples of such diseases include osteoporosis, arthritides, acquired immune deficiency syndrome (AIDS), burns, wounds such as bed sores and varicose ulcers, fractures, trauma, gastric ulceration, skin diseases such as acne and psoriasis, lichenoid lesions, epidermolysis bullosa, aphthae (reactive oral ulcer), dental diseases such as periodontal diseases, peri-implantitis, jaw cysts and other periapical cysts, dental conditions which are the target of root canal treatment or endodontic treatment, related diseases, external and intrinsic root resorption, caries etc.

The serine proteinases include human leukocyte elastase (HLE) and cathepsin G, and additional serine proteinases are involved in the cascade of pathways involved in connective tissue breakdown including but not limited to, plasmin, plasminogen activator, tumor-associated trypsins, etc.

MMP's and serine proteinases can work in combinations to bring about destruction of most of the elements of the extracellular matrix and basement membranes. As examples of the major interaction between MMP's and serine proteinases during tissue breakdown, 1) cathepsin G can activate MMP-8; 2) the serine proteinase Human Leukocyte Elastase (HLE) can inactivate TIMP's, the major endogenous Tissue Inhibitors of Matrix Metalloproteinases, 3) MMP-8 and MMP-9 can inactivate $\alpha_1$-Proteinase Inhibitor ($\alpha_1$-PI), the major endogenous inhibitor of human leukocyte elastase, (S. K. Mallya, et al., *Annuals of the New York Academy of Science,* 1994, 732:303–314) and 4) tumor-associated-trypsin-2 can efficiently activate latent pro MMP's (Sorsa et al., *J. Biol. Chem.* 1997, 272:21067–21074).

Tetracyclines, including chemically modified tetracyclines, can inhibit MMP-mediated tissue breakdown in vitro and in vivo, in part by binding to metal ions (calcium or zinc) in the MMP molecular structure. See, e.g., R. F. Zernicke et al., *Journal of Rheumatology,* 1997, 24:1324–31; T. Sorsa et al., *Journal of Rheumatology,* 1998, 25:975–82; Golub et al., *Adv. Dental Research* 1998, in press.

Certain tetracyclines have been shown to suppress matrix metalloproteinases independently of tetracycline antibiotic activity. U.S. Pat. No. 5,459,135 to Golub et al., U.S. Pat. No. 5,321,017 to Golub et al., U.S. Pat. No. 5,308,839 to Golub et al., U.S. Pat. No. 5,258,371 to Golub et al., U.S. Pat. No. 4,935,412 to McNamara et al., U.S. Pat. No. 4,704,383 to McNamara et al., U.S. Pat. No. 4,666,897 to Golub et al., and RE 34,656 to Golub et al. describe the use of non-anti microbial tetracyclines to treat tissue-destructive conditions, chronic inflammation, bone destruction, cancer and other conditions associated with excess activity of matrix metalloproteinases such as collagenases, gelatinase, and MMP-12 (macrophage metalloelastase).

U.S. Pat. No. 5,773,430 to Simon et al. describes using hydrophobic tetracyclines to inhibit excess leukocyte elastase serine proteinase activity in a biological system.

Tetracyclines are a class of compounds which are particularly well known for their early and spectacular success as antibiotics. Compounds such as tetracycline, sporocycline, etc., are broad spectrum antibiotics, having utility against a wide variety of bacterial and other microbes. The parent compound, tetracycline, has the following general structure:

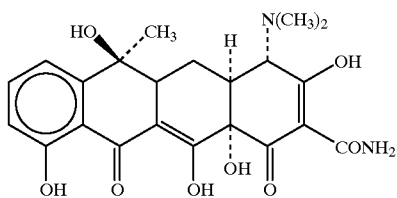

The numbering system of the multiple ring nucleus is as follows:

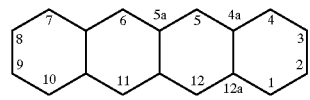

Tetracycline, as well as the 5-OH (oxytetracycline, e.g., terramycin™) and 7-Cl (chlorotetracycline, e.g. aureomycin™) derivatives, exist in nature, and are all well known antibiotics. Semisynthetic tetracyclines include, for example, doxycyline, minocycline and methacycline. The use of tetracycline antibiotics, while generally effective for treating infection, can lead to undesirable side effects. For example, the long-term administration of antibiotic tetracyclines can reduce or eliminate healthy flora, such as intestinal flora, and can lead to the production of antibiotic resistant organisms or the overgrowth of yeast and fungi. These significant disadvantages typically preclude treatment regimens requiring chronic administration of these compounds.

Natural tetracyclines may be modified without losing their antibiotic properties, although certain elements of the structure must be retained to do so. A class of compounds has been defined which are structurally related to the antibiotic tetracyclines, but which have had their antibiotic activity substantially or completely extinguished by chemical modification. The modifications that may and may not be made to the basic tetracycline structure were reviewed by Mitscher, L. A., *The Chemistry of the Tetracycline Antibiotics,* Marcel Dekker, New York (1978), Ch. 6. According to Mitscher, the modification at positions 5–9 of the tetracycline ring system can be made without causing the complete loss of antibiotic properties. However, changes to the basic structure of the ring system, or replacement of substituents at positions 1–4 or 10–12, generally lead to synthetic tetracyclines with substantially less, or essentially no, antibacterial activity.

Chemically modified tetracyclines (CMT's) include, for example, 4-de(dimethylamino)tetracycline (CMT-1), tetracyclinonitrile (CMT-2), 6-demethyl-6-deoxy-4-de(dimethylamino)tetracycline (CMT-3), 7-chloro-4-de(dimethylamino)tetracycline (CMT-4), tetracycline pyrazole (CMT-5), 4-hydroxy-4-de(dimethylamino)tetracycline (CMT-6), 4-de(dimethylamino)-12α-deoxytetracycline (CMT-7), 6-deoxy-5α-hydroxy-4-de(dimethylamino) tetracycline (CMT-8), 4-de(dimethylamino)-12α-deoxyanhydrotetracycline (CMT-9), 4-de(dimethylamino) minocycline (CMT-10).

Further examples of tetracyclines modified for reduced antimicrobial activity include the 4-epimers of oxytetracycline and chlorotetracyline (epi-oxytetracycline and epi-chlorotetracycline).

Bisphosphonates include a class of therapeutic preparations which have been used as bone resorption suppressants. U.S. Pat. No. 5,652,227 to Teronen et al. describes using bisphosphonates to reduce degradation of connective tissue matrix protein components which results from excess metalloprofeinase activity. U.S. Pat. No. 5,688,120 describes inhibiting alveolar bone resorption using iontophoretic delivery of bisphosphonates to alveolar bone by administering bisphosphonate in a reservoir connected to gingival tissue and passing an electrical current therethrough.

There has been no suggestion to use tetracyclines and bisphosphonates together in combination for the purpose of reducing, inhibiting, and down-regulating excess endogenous proteinase activity and to reduce destruction of tissues, basement membrane and other factors.

It is an object of the invention to provide a combination of compounds to treat subjects susceptible to proteinase related tissue damage and destruction.

SUMMARY OF THE INVENTION

A composition is provided for inhibiting, reducing, and down-regulating excess proteinases, thus treating or preventing proteinase-related connective tissue and basement membrane degradation in a biological system susceptible to structural and functional disturbances due to an excess of proteinase activity. The composition includes a tetracycline and a bisphosphonate. The inhibition involves reducing the amount and activity of proteinases and down-regulating the endogenous production of the proteinases. The composition of the invention can treat or prevent diseases related to proteinase imbalance by downregulating, preventing, or reducing excess activity of MMP's, serine proteinases, MMP-like and related enzymes such as the tumor necrosis factor converting enzyme (TACE)-dependent tumor necrosis factor alpha (TNFα) activation, and membrane proteins with a disintegrin and metalloproteinase domain (ADAM's).

The degradation treated according to the invention can involve hard and soft tissues including connective tissue and basement membranes. The degradation can be associated with conditions such as bone resorption, cartilage destruction or destruction of soft tissues, and tissue invasion and metastasis by malignant cells. The structural and functional disturbances include as non-limiting examples, loss of teeth due to periodontal breakdown and fracture of skeleton due to excess bone destruction, for example, during osteoporosis. Excess proteinase is inhibited by a reduction in the amount and activity of proteinase and downregulating of the proteinase production. Down-regulating means blocking the gene expression and secretion of the proteinase, i.e., decreasing the synthesis and release of the enzyme protein. The therapy can also block the activity or activation of the proteinases independent of an effect on enzyme synthesis.

The composition can be in the form of a pharmaceutical or cosmetic preparation and therefore the composition can be included with a pharmaceutical or cosmetic preparation or carrier.

The composition preferably comprises a combination of tetracycline and bisphosphonate in synergistic amounts for inhibiting excess proteinase activity so that the combination exhibits synergy in the efficiency of inhibiting, reducing and down-regulating of proteinases involved in tissue breakdown. This means that the combination is more effective than either tetracycline alone or bisphosphonate alone and the efficiency of the combination is generally greater than that expected by adding the two effects.

In a method for inhibiting and/or reducing the activity of, and down-regulating excess proteinases and related breakdown of connective tissue, basement membranes and other factors reflecting functional and structural disturbances in a biological system susceptible to this tissue breakdown, a composition which includes a combination of tetracycline and bisphosphonate is administered to the system in proteinase inhibiting, reducing and/or down-regulating amounts.

DETAILED DESCRIPTION OF THE INVENTION

Figure 1:
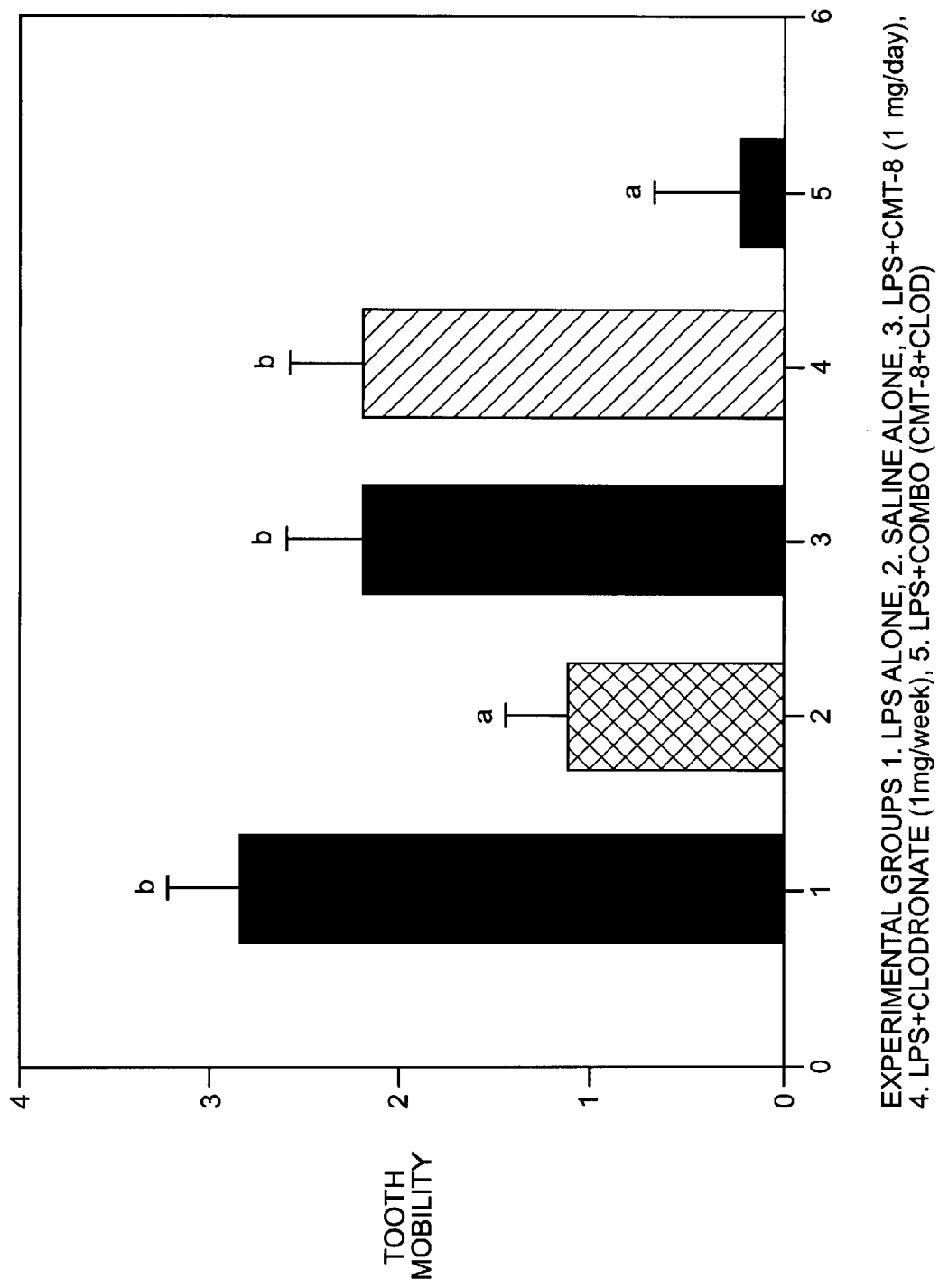
FIG. 1 is a bar graph illustrating Tooth Mobility results in Example 3.

The invention includes a composition and method for inhibiting tissue destructive conditions associated with excess production and activity of connective tissue and basement membrane degrading proteinases, e.g., metalloproteinases, metalloproteinase-like and related enzymes, serine proteinases and other proteinases, as well as microbial, viral and fungal proteinases. Application of the composition of the invention to a subject in need of treatment inhibits or prevents breakdown of connective tissue, basement membranes, and other disease processes.

The tissue destructive conditions which can be treated and/or prevented with the present invention result from excess proteinase activity of metalloproteinases, metalloproteinase-like proteinases and related proteinases, serine proteinases or combinations of these enzymes, as well as microbial, viral and fungal proteinases. These conditions include, e.g., tissue invasion by malignant cells, bone resorption, cartilage destruction, destruction of soft tissues (e.g., skin, tendons, ligaments, blood vessel walls, etc.), as well as tumor spread and cancer metastasis to both soft and hard tissues, and bronchiectasis, chronic destructive and obstructive lung disease, asthma, and other lung diseases. Mammalian diseases such as periodontitis, osteoarthritis, rheumatoid arthritis, reactive and other arthritides, cancer invasion and metastasis, osteomyelitis, osteoporosis, osteosarcoma, and other bone diseases can be advantageously prevented and/or treated. While it is not intended to be bound by theory, the treatment may be effective at least in part because both the CMT's and the bisphosphonates are bone-seeking pharmacologic agents. The combination also can be used to treat tissue-destructive diseases in pets (cats, dogs, etc.) and large mammals such as horses and other mammals.

Particular tissue and basement membrane destructive conditions treated according to the invention include as non-limiting examples, bone diseases such as osteoclast-mediated bone resorption, and disorders involving cellular passage through basement membranes such as cancer metastases and lymphocyte infiltration, e.g., in the islets of Langerhans related to the onset of Type-1 diabetes.

The composition of the invention can be linked to pharmaceutical preparations containing molecules that target sites such as tumor tissue, metastasis, and/or vasculature for delivery thereto. Examples of these molecules are homing peptides (W. Arap et al., Science 1998, 279:377–380).

A need for treatment can be estimated from or based on various clinical, radiological and biochemical parameters of disease severity. One example for arthritis diseases includes clinical signs of joint pain and weakness, x-ray evidence of bone and cartilage destruction and detection of elevated levels of collagen crosslink (pyridinoline and deoxypyridinoline) fragments in serum and urine indicating increased bone and cartilage collagen breakdown. A diagnosis of periodontitis and peri-implantitis includes, e.g., clinical evidence (e.g., increased depth of periodontal pockets; loss of periodontal and peri-implant attachment), microbiological, biochemical, immunological and/or molecular biology evidence of periodontal tissue breakdown.

Connective tissue forms the extracellular matrix which connects and supports other tissues in all parts of the body. Connective tissue includes collagenous (white fibers in skin, tendon, bone, cartilage, etc. made up of coiled protein fibrils), elastic (yellow fibers of albuminoid scleroprotein), mucous, reticular (net-like), osseous (bone), and cartilagenous (chondrocytes embedded in chondrin and including hyaline (clear), elastic or fibrocartilage) and sometimes blood vessels/components (endothelial cells, e.g., which proliferate at a site of inflammation). Connective tissue may be further classified as loose (areolar) and dense (more fibrous).

The basement membrane is a membrane of modified connective tissue beneath epithelial tissue, as of a gland containing acini or special secreting portions. The basement membrane is a complex structure comprised of type IV collagen, heparan sulfate proteoglycan and laminins, which attaches the epithelium to the underlying connective tissue. After basement membrane destruction to overcome extracellular matrix barriers, specific cleavage of laminin-5 by gelatinases (Giannelli et al., Science 1997, 277:225–228) is required for inflammatory and malignant cell migration. The present combination of tetracycline and bisphosphonate inhibits this also.

In one embodiment, the composition of the invention is used to treat MMP-dependent conditions. MMP-dependent conditions include, for example, wounds, burns, fractures, lesions, trauma, ulcers, cancer and metastasis progression in connective tissues and bone; other conditions include periodontitis, gingivitis, peri-implantitis, jaw cysts, internal and external root resorption, caries, AIDS, corneal ulceration, gastric ulceration, aphthous ulcers, acne, psoriasis, loosening of hip prosthesis, osteomyelitis, osteoporosis, tissue remodeling, angiogenesis, arthritides (rheumatoid, reactive and osteo arthritis), lung diseases (bronchiectasis and chronic obstructive pulmonary diseases and other lung diseases).

Tetracyclines in combination with bisphosphonate have been found to inhibit the production and/or activity of endogenous proteinases in a biological system.

The preferred tetracyclines are 4-de(dimethylamino) tetracycline (CMT-1), 6-demethyl-6-deoxy-4-de (dimethylamino)tetracycline (CMT-3), 6-deoxy-5-alpha-hydroxy-4-de(dimethylamino)tetracycline (CMT-8), also, doxycycline, minocycline, lymecycline and combinations of the tetracyclines.

Bisphosphonates are compounds related to inorganic pyrophosphonic acid and are commercially available or can be prepared according to known methods. The bisphosphonates useful herein include as non-limiting examples, e.g., alendronate ((4-amino-1-hydroxybutylidene)bisphosphonic acid), clodronate(dichloromethane diphosphonic acid), etidronate ((1-hydroxyethylidene)disphosphanic acid) and pamidronate ((3-amino-1-hydroxypropylidene) bisphosphonic acid); also risedronate ([-hydroxy-2-(3-pyridinyl)ethylidene]bisphosphonic acid), tiludronate, i.e., tiludronic acid ([(4-chlorophenyl)thio]methylene] bisphosphonic acid) and zolendronate.

Others include [1-hydroxy-3-(methylpentylamino) propylidene]bis-phosphonate (BM21.0955), [(cycloheptylamino)methylene]bisphosphonate (YM175), 1-hydroxy-3-(1-pyrrolidinyl)-propylidene]bisphosphonate (EB-1053), [1-hydroxy-2-(1H-imidozol-1-yl)ethylidene] bisphosphonate (CGP 42'446) and (1-hydroxy-2-imidazo-[1,2-a]pyridin-3-yl-ethylidene)bisphosphonate (YM 529).

Bisphosphonates are comprehensively described by H. Fleisch, Endocr. Rev., 1998, 19(1):80–100; see also, H. Fleisch, Bisphosphonates in Bone Disease: From the Laboratory to the Patient, 1997, 3rd Edition. The Parthenon Publishing Group, New York and London.

The preferred bisphosphonates are alendronate, clodronate (clodrinate), etidronate, pamidronate, medronate, nedrinate, tiludronate, zolendronate and combinations thereof.

The amount of each compound in the composition of the invention including tetracycline and bisphosphonate for use in a specified case will vary depending on the particular composition formulated, the mode of application, the subject, the site to which the composition is administered, the degradative condition being treated or prevented, and the mode of administration. Dosages will be determined using conventional consideration, e.g., by customary comparison of the differential activities of the formulations and of a known agent, e.g., by means of an appropriate conventional pharmacologic protocol. Typical doses for human use include 10–1000 mg/day tetracycline in combination with 20–2000 mg/day bisphosphonate depending upon type of bisphosphonate and route of administration. The amounts of the tetracycline and the bisphosphonates useful in the invention are amounts which in combination result in an inhibition of the activity and/or secretion and synthesis of excess proteinase in a system or subject susceptible to excess proteinases. These amounts are advantageously as much as ten-fold less than amounts which are optimal or needed when each compound is used alone, thereby significantly reducing the possibility of side-effects caused by higher doses if the compounds were to be taken individually, e.g., when using individual compounds, 10–30 $\mu$M is needed; together 2.0–10.5 $\mu$M is needed.

For oral administration, the composition of the invention may be formulated in the form of tablets, capsules, elixirs, suspensions, solutions, or the like. For parenteral administration, the composition may be formulated into injectable forms such as solutions or suspensions, e.g., for intramuscular injection. For topical application, the composition may be applied directly or incorporated with a delivery system such as a carrier or substrate, e.g. a polmer, or formulation into a cream, ointment, aerosol, membranes, etc.

The activity of combinations of various tetracyclines and bisphosphonates was investigated in vivo. The animal model of disease used was published previously (Ramamurthy et al., *Archs. Oral Biol.,* 1985, 130:679–683) and involves the injection of endotoxin (i.e. bacterial lipopolysaccharide (LPS), a major structural component of the outer membrane of gram-negative bacteria, and a major mediator of inflammation and bone destruction during periodontitis and other infections) directly into the gingiva of rats every two days over a 7-day time period. This procedure produces marked inflammation in the periodontal tissues and induces elevated levels of tissue-destructive matrix metalloproteinases (MMPs) and serine proteinases such as elastase in the gingiva leading to severe alveolar bone resorption and bone loss around the affected teeth, all within the 7-day experimental protocol. In brief, adult male rats with this experimentally-induced inflammatory disease were either left untreated, or treated with sub-optimal doses of (I) a CMT by itself; (II) a bisphosphonate by itself, or (III) a combination of (I) and (II). At the end of the experimental protocol, tooth mobility and alveolar bone loss, and levels of various tissue destructive MMP collagenases and gelatinases and serine enzymes in the gingiva, were measured. Suboptimal doses of either the CMT by itself or the bisphosphonate by itself produced little or no reduction in these parameters of soft and hard tissue destruction. In contrast, the combination of these two type of drugs synergistically reduced the pathologic levels of these destructive pathways, often reducing these levels in the endotoxin-injected tissues to the normal levels of collagenases, gelatinases and elastase seen in the saline-injected (control) tissues.

The combination was also tested in vitro in cultured chicken osteoclasts (bone resorbing cells) and showed inhibition of osteoclast gelatinase activity.

The combination was also tested in vitro in human fibrosarcoma cells and against human recombinant $MT_1$-MMP (MMP-14) and pure wild-type MMP-8. In brief, we tested the effects of suboptimal MMP-inhibitory concentrations of CMT (-3 and -8) and clodronate (clodrinate) on the in vitro migration of HT-1080 fibrosarcoma cells using a Transwell-assay system. As a result of different tumor-promoting inductions, human fibrosarcoma cells of cell line HT-1080 express and activate both extracellular MMP's (MMP-2, -9) and cell-surface bound MT-MMP's, which participate in an activation cascade in malignant invasive and metastatic as well as angiogenic processes. H. Birkedal-Hansen, *Curr. Op. Cell Biol.* 1995, 7:728–735; D. Hanahan et al., *Cell* 1996, 86:353–364.

Also, suboptimal inhibitory doses of CMT's and bisphosphonate, alone and in combination, were tested on pure human recombinant $MT_1$-MMP and MMP-9 activities using a β-casein-degradation assay. The assay is described by Teronen et al., *J. Dent Res.* 1997, 76:1529–1537; T. Sorsa et al., *J. Biol. Chem.* 1997, 272:21067–21074. Suboptimal doses of either CMT's alone or bisphosphonates alone caused little or no reduction in the HT-1080 migration and only slightly inhibited $MT_1$-MMP activities. However, the combination of CMT's and bisphosphonates synergistically reduced the in vitro migration of HT 1080 fibrosarcoma cells as well as inhibited the activities of the pure human recombinant MT-1-MMP.

In vivo and in vitro experiments demonstrate that a combination of a chemically-modified non-antibacterial tetracycline plus a bisphosphonate synergistically inhibits connective tissue (including bone) and basement membrane breakdown as well as malignant cell migration and synergistically inhibits the activities of pure human cell bound $MT_1$-MMP and extracellular collagenases, gelatinases (extracellular MMP's) as well as elastase (serine proteinase).

For in vivo Examples, Thirty male Sprague-Dawley rates were distributed into 5 groups as follows:
Group 1: Normal. Saline injected+placebo therapy (CMC)
Group 2: LPS. LPS injected+placebo (CMC)
Group 3: CMT-8. LPS injected+CMT-8 (1 mg/day)
Group 4: Clodronate. LPS injected+Clodronate (1 mg/week)
Group 5: Combo. LPS+CMT-8 (1 mg/day)+Clodronate (1 mg/week)

The treatments were administered by oral gavage once per day (CMT-8) throughout the entire 7 day period, or by a single subcutaneous injection (clodrinate).

LPS (lipopolysaccharide)-induced periodontitis rat model: Twenty four hours before treatment, the rats were injected into the upper anterior gingivae and into the palatal papillae between 1st and 2nd upper molars with 10 µL of LPS (1 mg/ml) or saline solution, for a total of 10 µg LPS per site injected. The LPS injections were repeated every other day to complete the three injections.

On day 7, all rats were anesthetized, blood samples were collected by cardiac puncture and rats were sacrificed. Tooth mobility was checked and the gingival tissue was dissected and stored at −80° C. for subsequent enzyme analysis. The jaws were defleshed for bone loss determination.

EXAMPLE 1

The first experiment was designed to select sub-optimal doses of both CMT-8 (a chemically-modified, non-antibacterial tetracycline) and clodronate (a bisphosphonate) in the endotoxin-induced bone loss model. Groups of rats (n=5–6rats/group) were anesthetized and injected directly into the gingival tissues with either saline (control group) or with LPS endotoxin every other day over a 7-day time period. Twenty-four hours after the first injection, groups of rats were administered by oral gavage either 0, 0.5 mg, 1 mg, or 2 mg CMT-8 daily for the next 6 days. At the end of the experiment, the rats were anesthetized, blood was drawn by intracardiac puncture, the rats were euthanized and the gingival tissues dissected for enzyme analysis. In addition, tooth mobility was scored and, after defleshing the jaws, alveolar bone loss around the teeth was scored morphometrically using a computer-assisted system. The results are discussed below.

EXAMPLE 2

In a second experiment, a similar protocol was used to identify the sub-optimal dose of clodronate in this model, except the different doses of this drug (0, 0.5 mg. 1 mg, 2 mg) were administered by a single subcutaneous injection.

Based on the above experiments of EXAMPLES 1 and 2, the results showed that 0.5 mg of either CMT-8 or clodronate produced no significant effects on tooth mobility and alveolar bone loss; in contrast, 2 mg of either drug essentially returned the pathologic tooth mobility and bone loss, induced by bacteria endotoxin, to control levels. Therefore, 1 mg of either drug was selected as the sub-optimal dose because it produced either no, or barely detectable beneficial effects.

EXAMPLE 3

In a third experiment, 30 adult male rats were distributed into the following experimental groups: saline-injected group; groups injected with endotoxin and then administered no drug, CMT-8 alone (1 mg/day), clodronate alone (1 mg/week), or a combination of the same sub-optimal doses of both drugs. The experiment was terminated on day 7. As described above, the gingival tissues were dissected, extracted and the partially-purified extracts analyzed for neutral proteinase (elastase and matrix metalloproteinase) activities, and both tooth mobility and alveolar bone loss were assessed.

Figure 2:
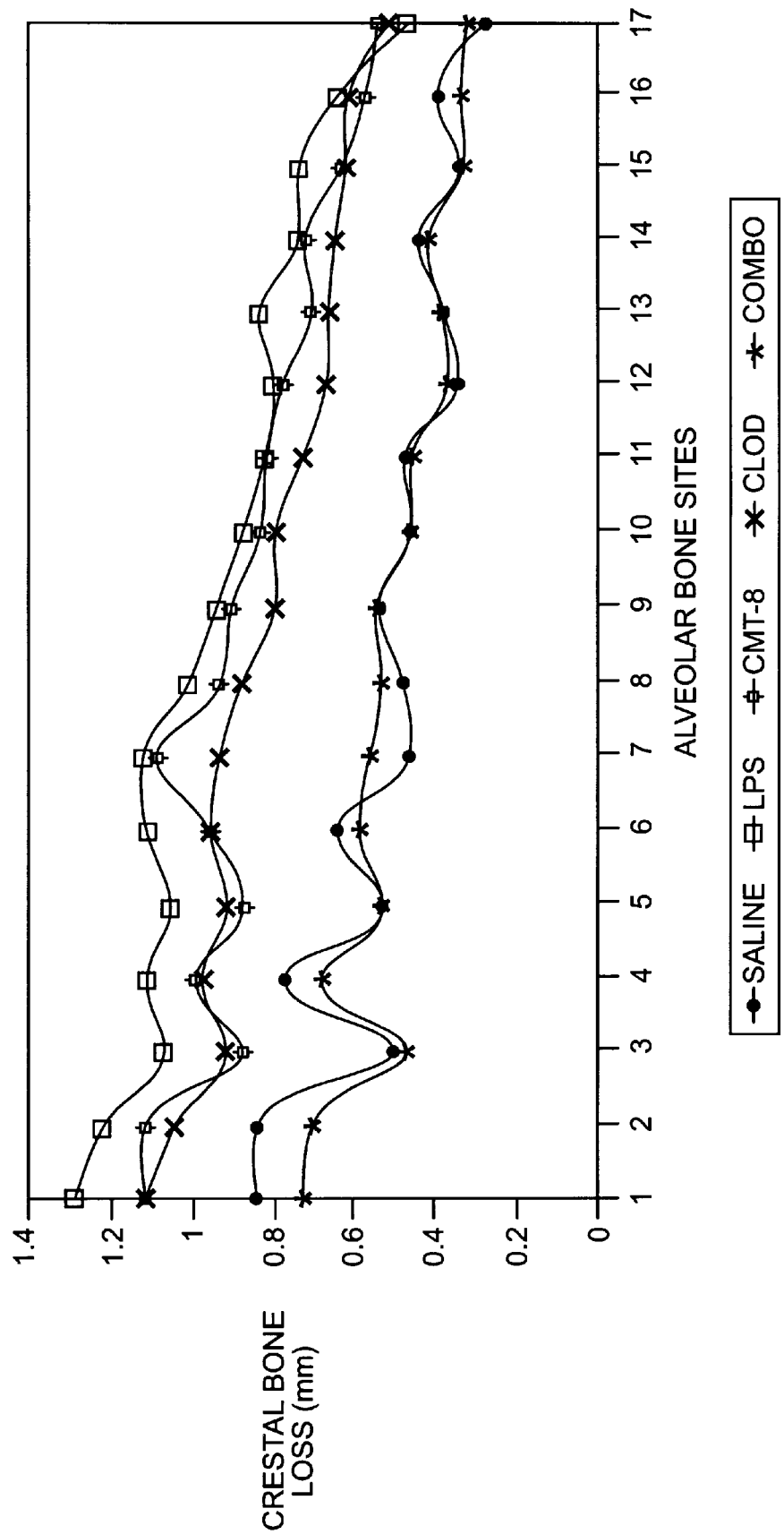
FIG. 2 is a bar graph illustrating Aveolar Bone Loss results in Example 3.
Figure 3:
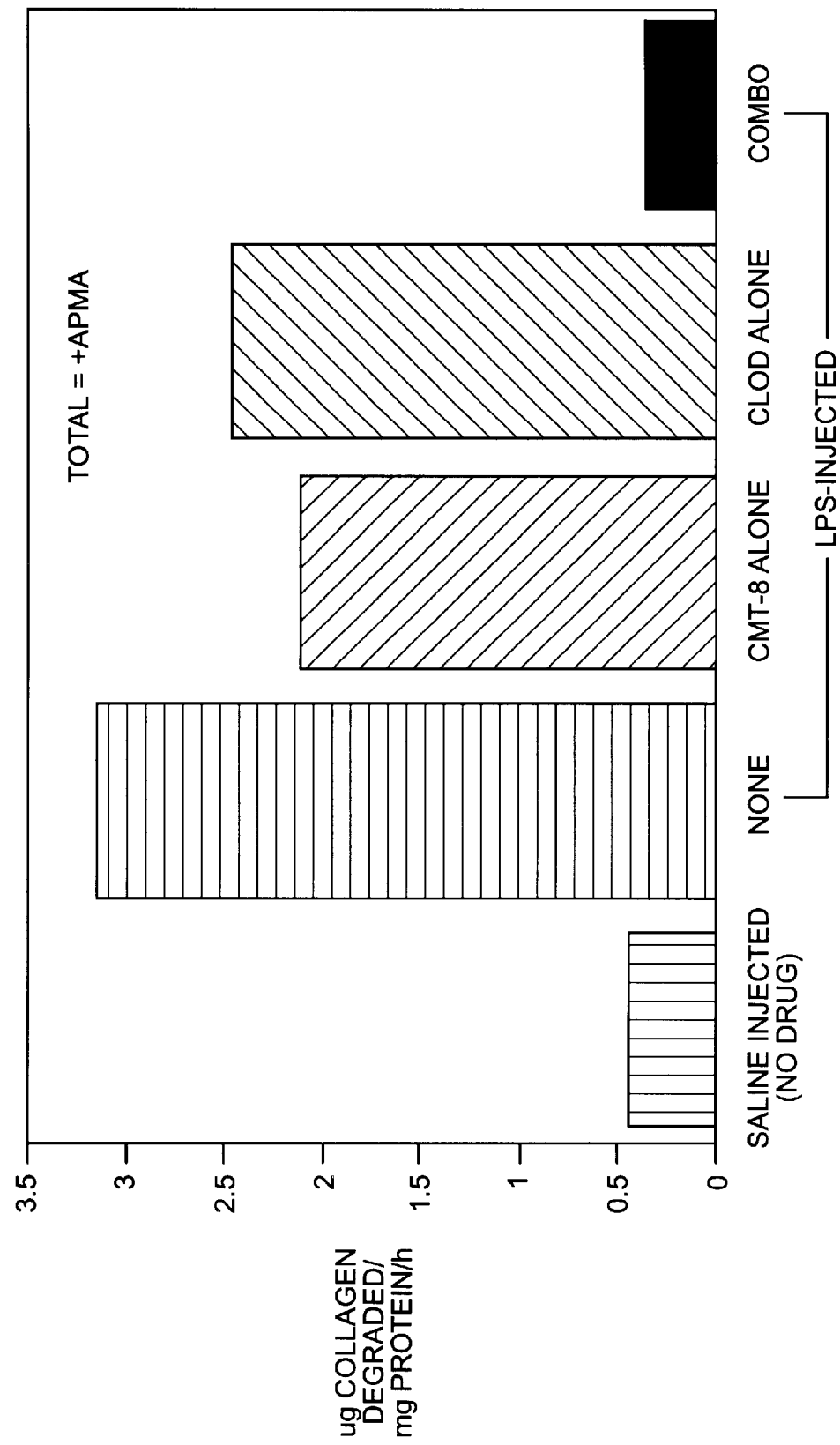
FIG. 3 is a bar graph illustrating Effect on Gingival Collagenase activity in Example 3.
Figure 4:
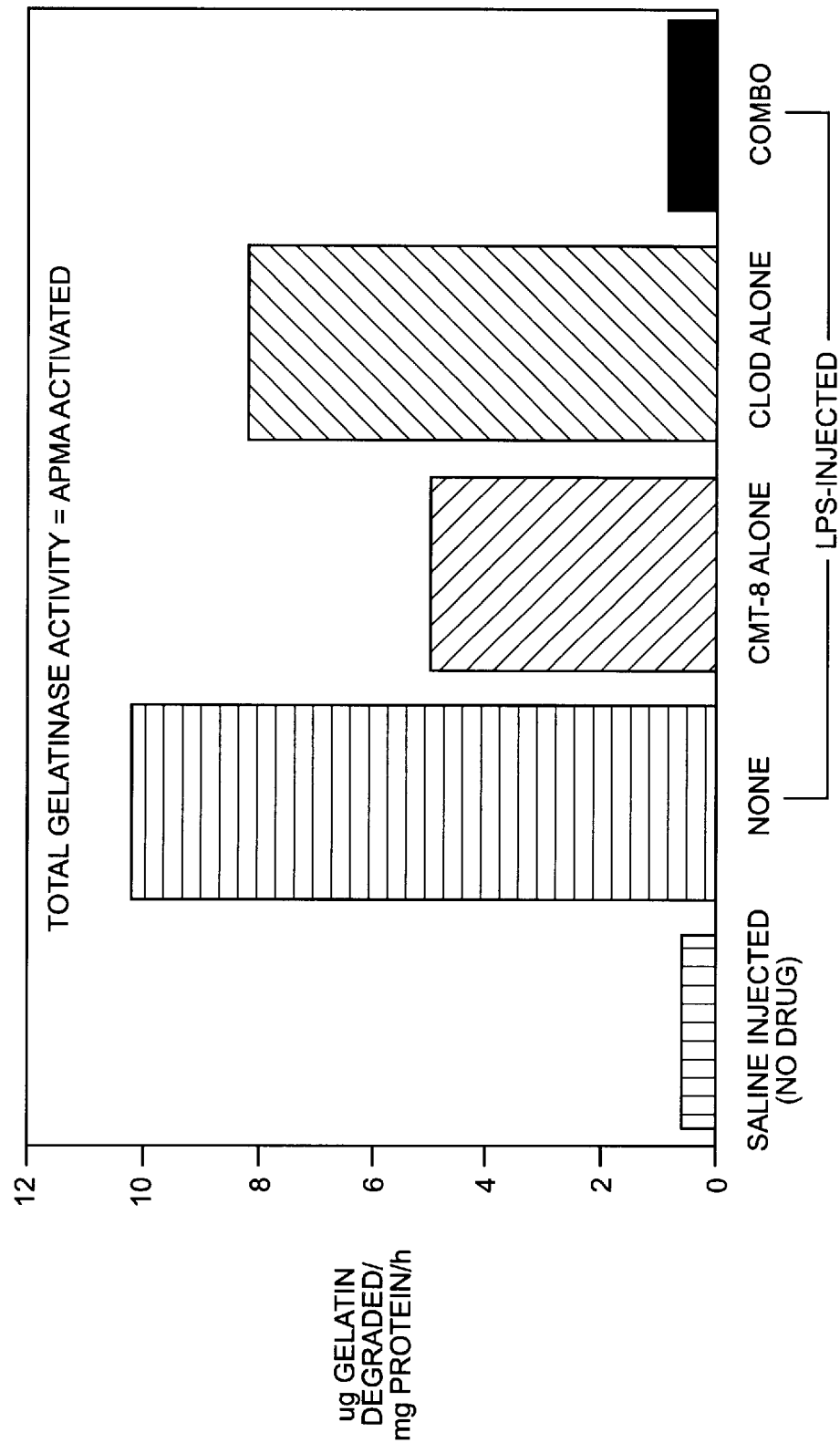
FIG. 4 is a bar graph illustrating Effect on Gingival Gelatinase activity in Example 3.

Tooth mobility results are shown in FIG. 1. Aveolar bone results are shown in FIG. 2. The effect on Gingival Collagenase activity is shown in FIG. 3. The effect on Gingival Gelatinase activity is shown in FIG. 4.

In FIG. 1, tooth mobility is based on the following scoring system:
0=no movement
1=slight movement (vestibule-palatal)
2=medium movement (vestibule-palatal)
3=severe movement (vertical mobility in and out of socket)
a vs b, p<0.05
a vs a, (N.S.) (Not Significant)
b vs b, (N.S.)

As shown in FIG. 1, tooth mobility (a reflection of severity of inflammation and collagen loss in the periodontal tissues plus alveolar bone loss) was very severe in the untreated LPS-injected rats (Group 1) compared to the saline-injected rats (Control; Group 2). When the LPS-injected rats were treated with sub-optimal CMT-8 by itself (Group 3) or sub-optimal clodronate by itself (Group 4), only very slight (not statistically significant) reductions (18%) in tooth mobility were seen and the tooth mobility in these groups, Groups 3 and 4, was still more than twice the level seen in the control rats (Group 2). However, when the LPS-injected rats were treated by the combination of the two drugs (sub-optimal dose CMT-8 plus sub-optimal dose clodronate), a synergistic reduction (89.3%; p<0.05) in tooth mobility was seen such that this parameter was even 70% lower than the tooth mobility seen in the salineinjected (control) group of rats.

Based on computer-assisted morphometric analysis of the defleshed rat jaws and as shown in FIG. 2, the rats in the LPS-injected group showed significantly greater alveolar bone loss at all 17 different sites in each half maxilla than the bone loss seen at the same 17 sites in the saline-injected control group. For example, at site #7, located interproximally between the 1st and 2nd molar teeth (a site which generally shows most severe bone loss in these rat models of periodontal disease), LPS-injection into the gingiva increased alveolar bone loss, compared to saline injection, by 140%. Treating the LPS-injected rats with either CMT-8 alone or clodronate alone reduced alveolar bone loss only slightly, if at all. In sharp contrast, the combination therapy essentially "normalized" the alveolar bone loss, induced by bacterial endotoxin (LPS), so that the bone loss levels were the same as those seen in the saline-injected control rats.

Collagenase activity in partially-purified extracts of gingiva from the different groups of rats was assessed using [$^3$H-methyl] collagen as the substrate, separating the intact $\alpha_1$ and $\alpha_2$ collagen components and the collagenase-generated ¾ breakdown products of collagen ($\alpha_1^A$ and $\alpha_2^A$) by SDS-PAGE, visualizing these collagen components and fragments by autoradiography, and calculating their levels after scanning the fluorograms with a laser densitometer. The data shown in FIG. 3 represents the total collagenase activity in the gingival extract samples after activating any pro-collagenase (latent) in the samples by the addition of 1.2 mM amino phenylmercuric acetate (APMA). As shown in FIG. 3, injecting the gingiva with LPS dramatically increased collagenase activity by 700%, consistent with this MMP being responsible, at least in part, for the breakdown of type I collagen, the major constituent of all of the periodontal tissues including the bone matrix. Treatment of the LPS-injected rats with either CMT-8 alone or clodronate alone (CLOD) reduced collagenase activity slightly by 22–31%. In contrast, and like the effect on tooth mobility and alveolar bone loss, combination therapy (COMBO) synergistically reduced collagenase by 91%, down to the levels seen in the saline-injected control-group gingival tissues.

Gelatinase activity was measured by a modification of the method of McCroskery et al., "Purification and Characterization of a Collagenase Extracted From Rat Tumors", Biochem. J., 1975, 182:131–142, incubating aliquots of the different gingival extracts with [$^3$H-methyl] gelatin as the substrate. After the incubation at 37° C., the release of solubilized degradation products was measured by liquid scintillation spectrometry. As demonstrated by the results in FIG. 4, Gelatinase activity (which like collagenase, was measured after APMA-activation of latent pro-forms of this MMP) showed the same pattern of change as collagenase for the different groups of rats; combination therapy again produced a synergistic reduction in the excessive levels of this MMP in the gingival tissues of LPS-injected rats.

Similar patterns of change for these tissue-destructive enzymes were seen for the following:
zymography to assess different molecular species of gelatinase
elastase activity was measured spectrophotometrically using a synthetic peptide substrate specific for neutrophil (inflammatory cell) elastase.
MMP-2 (gelatinase A), MMP-9 (gelatinase B), MMP-8 (collagenase-2) and MMP-13 (collagenase-3) were all detected by Western blot analysis using specific antisera (T. Sorsa et al., Ann. N.Y. Acad Sci. 1994, 732:112–131; L. M. Golub, et al., Infl. Res. 1997, 36:310–317). It is noteworthy that all of these assays demonstrated synergistic inhibition of the activities of these MMP-proteinases and elastase as well as the down-regulation of the level of these enzymes due to combination (CMT plus bisphosphonate) therapy.

EXAMPLE 4

Cell Culture Experiments Demonstrating That a Combination of a Chemically-Modified Tetracycline and a Bisphosphonate Inhibits Gelatinase Produced by Bone-Resorbing Cells (Osteoclasts) in Culture More Than Either Drug Alone.

Post-incubation media from cultured chicken osteoclasts were partially-purified, then incubated with [$^3$H-methyl] gelatin for 4 hours at 37° C. in the presence of 1.2 mM APMA to activate any latent Pro-gelatinase. The incubations were carried out in the presence (or absence) of several different concentrations (0.001–1000 μM) of a bisphosphonate, Didronel (Etidronic Acid); where appropriate, CMT-1 was added at a final concentration of 50 μM. After the 4 hour incubation, the reaction was stopped by the addition of 45% Trichloroacetic acid and carrier gelatin, the mixture was centrifuged, and aliquots of the supernatant, containing the radiolabeled gelatin degradation fragments, were counted in a liquid scintillation spectrometer.

Figure 5:
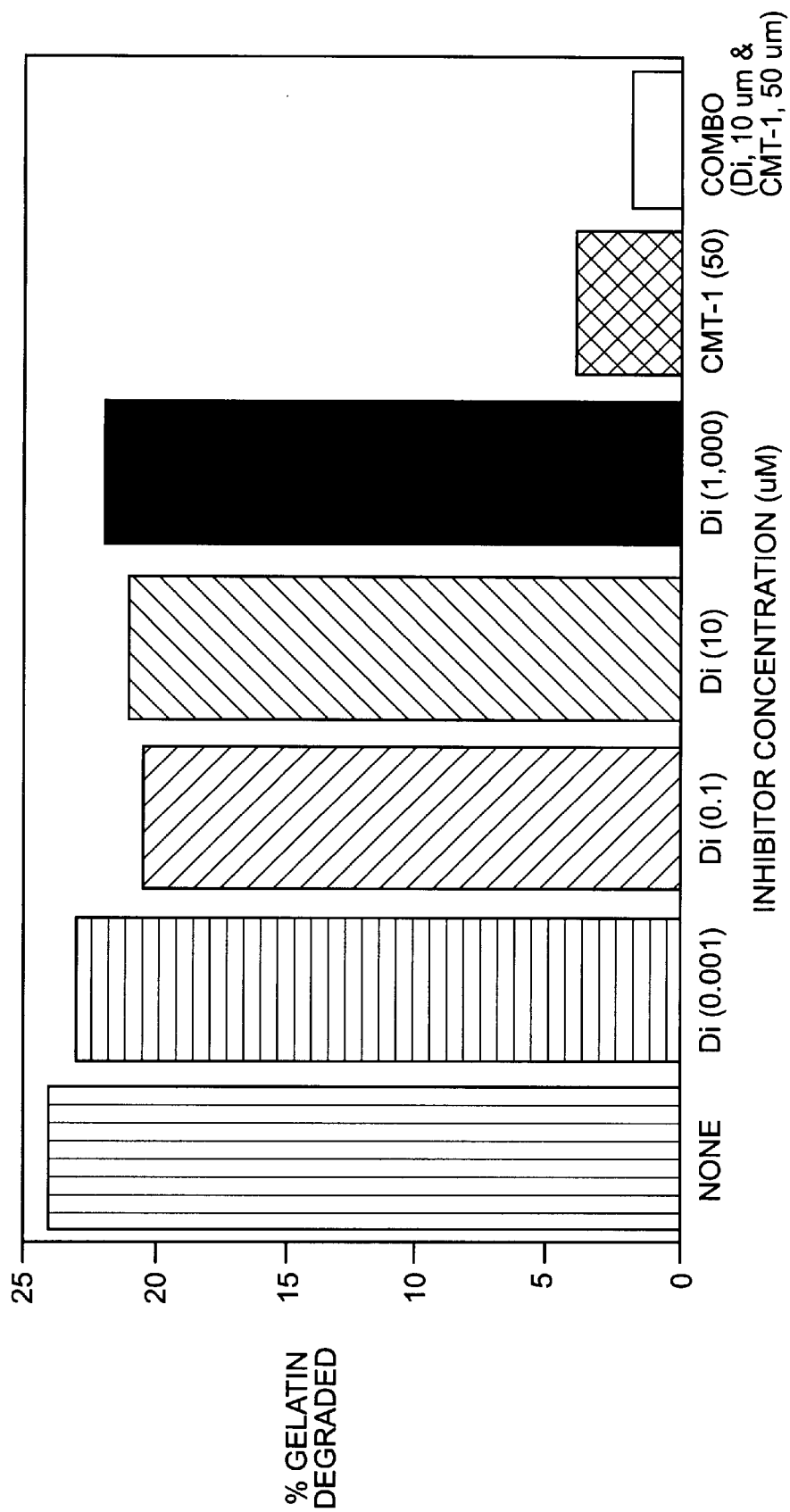
FIG. 5 is a bar graph illustrating the Inhibition of Osteoclast Gelatinase in Example 4.

The results are shown in FIG. 5. The 50 μM CMT-1 inhibited the osteoclast gelatinase activity by about 79%. Didronel, at 0.001, 0.1, 10, and 1000 μM final concentrations did not show any detectable inhibition of this enzyme.

However, when CMT-1 was combined with 10 μM of Didronel, the osteoclast activity was inhibited by 92%, more than seen with either drug alone.

EXAMPLE 5

Combinations of CMT-3 or CMT-8 and clodronate were tested for inhibition of cell migration in vitro of human HT-1080 fibrosarcoma cancer cells. HT-1080 cells were allowed to migrate in the presence of medium containing 10% serum for 18 h in Transwell chambers (Costar, Cambridge, Mass.). Random cell migration was studied using 8.0 μM pore size and 6.5 mm diameter Transwell inserts that were equilibrated in the 10% serum-containing medium 2 h before use. 750 μl of the serum containing media were added to lower compartments of the migration apparatus. For random migration assays, cells were preincubated for 2 h in the presence of the indicated concentrations. CMTs and clodronate alone or in combination and 20,000 cells in a volume of 100 μl were plated in a Transwell. After culturing for 18 hours the cells were fixed in methanol, washed and stained in toluidine blue. Cells were removed from the upper surface of the membrane with a cotton swab, and the cells which migrated on the underside of the membrane well were counted microscopically, or were alternatively quantitated by computer scanning.

Figure 6:
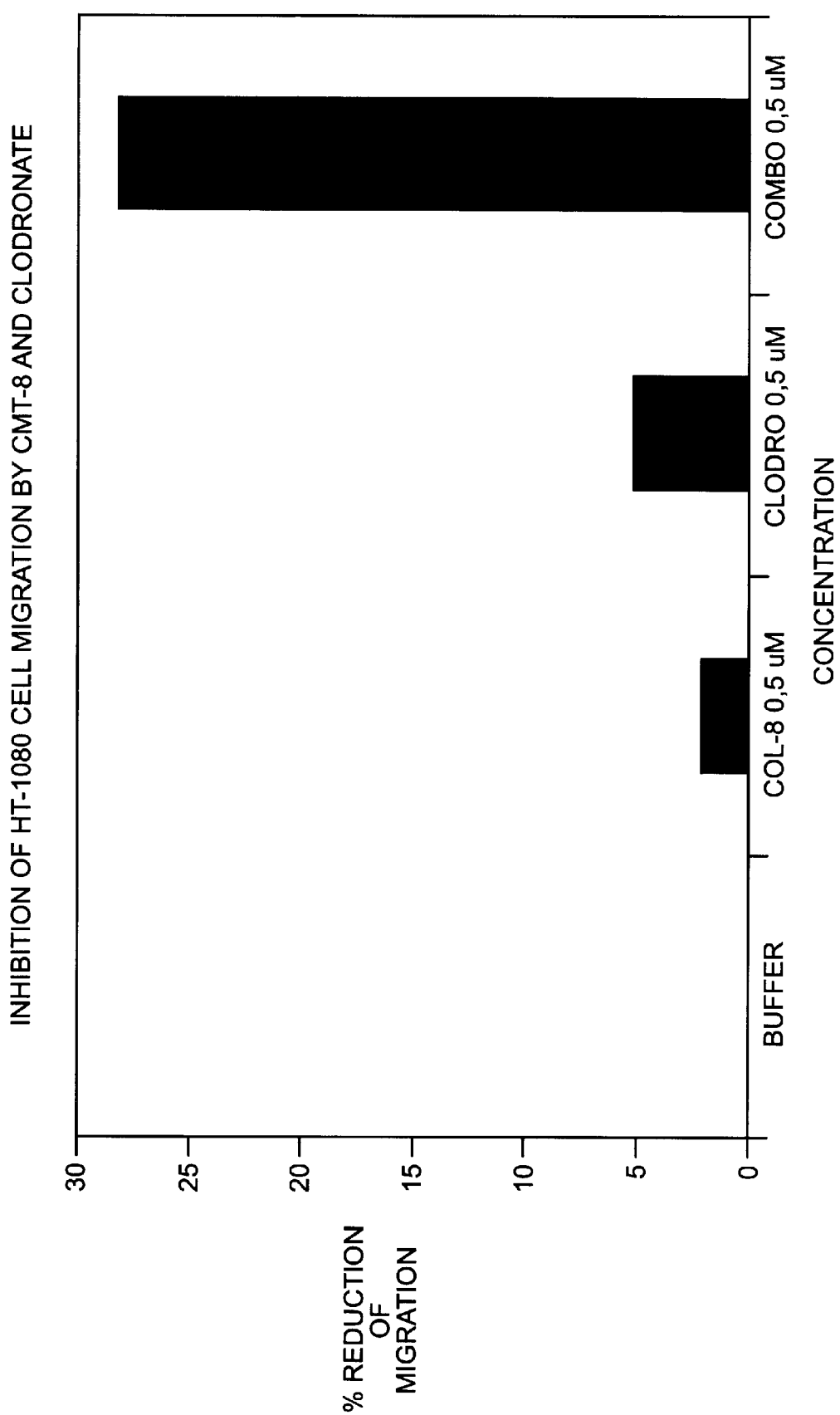
FIG. 6 is a bar graph illustrating the Inhibition of Cancer Cell Migration in Example 5.
Figure 7:
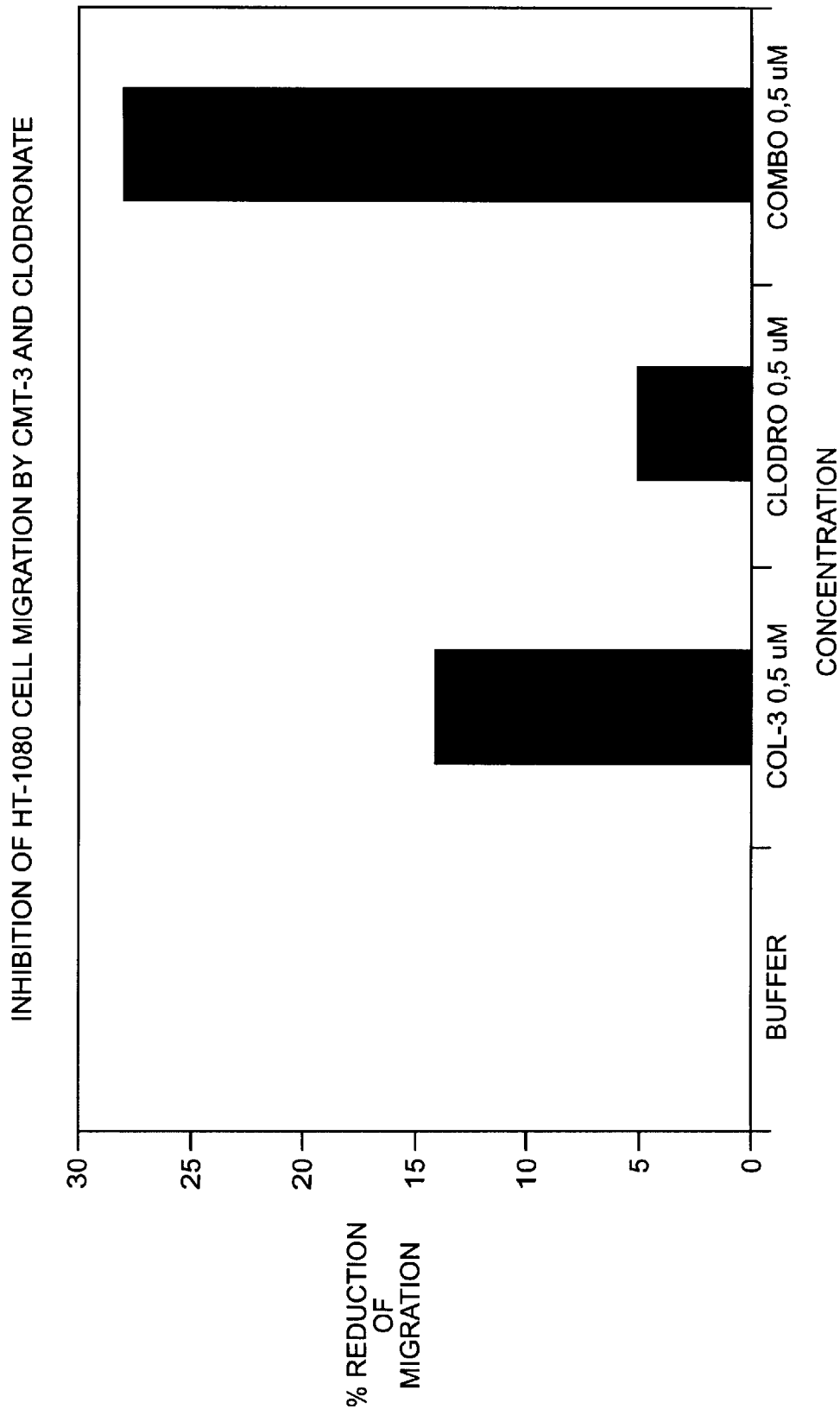
FIG. 7 is another bar graph illustrating the Inhibition of Cancer Cell Migration by another combination in Example 5.

The concentrations of the test combinations and results are shown in FIGS. 6 and 7. The results indicate that a combination of 0.5 uM amounts of either CMT-3 or CMT-8 together with 0.5 μM clodronate synergistically inhibited the cell migration.

EXAMPLE 6

Figure 8:
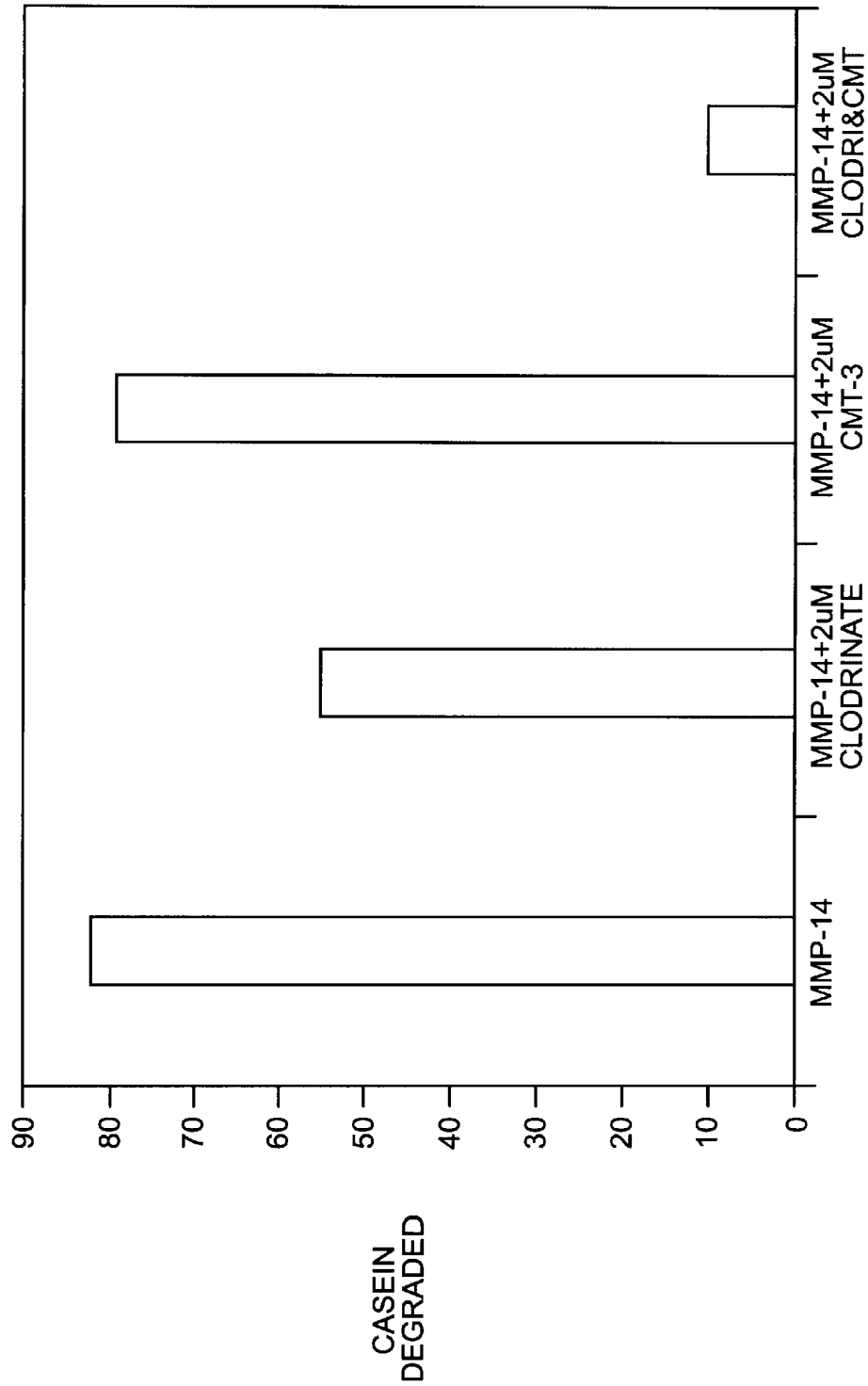
FIG. 8 is a bar graph illustrating the Inhibition of Casein Degradation by $MT_1$-MMP (MMP-14) in Example 6.

Recombinant human (50 mg) $MT_1$-MMP (also called MMP-14) (In Vitro-Tek, Berlin, Germany) was pretreated with buffer (none), 2 μM CMT-3 and 2 μM bisphosphonate clodronate (clodrinate) and combinations of 2 μM CMT-3 and 2 μM clodrinate for 1 h at 37° C., Subsequently, substrate P-casein (52 μM) was added to the incubation mixtures, and incubations continued for 60 min at 37° C. Incubation was terminated by adding Laemli's sample buffer and boiling for 5 min before SDS-PAGE and quantitative laser-densitometric analysis (Sorsa et al., *J. Biol. Chem.* 1997, 272:21067–21074; Teronen et al. *J. Dent Res.* 1997, 76:1529–1537. Combination of suboptimal doses of CMT-3 clodronate (clodrinate) resulted in synergistic inhibition of β-casein degration by pure recombinant human MT-MMP. The results shown in FIG. 8, indicate that combination of suboptimal 2 μM amounts of CMT and bisphosphonate (clodrinate) synergistically inhibited the activity of human MT-1-MMP in comparison to the relative slight inhibition by the CMT-3 or clodrinate alone.

We claim:

1. A composition for treating or preventing connective tissue and basement membrane degradation in a biological system susceptible to excess proteinase activity which comprises a synergistic mixture of a tetracycline and a bisphosphonate compound.

2. The composition of claim 1 wherein the degradation is related to excess proteinase activities.

3. The composition of claim 1 wherein the biological system is mammalian.

4. The composition of claim 1 further comprising a pharmaceutical preparation or carrier.

5. The composition of claim 1 wherein the proteinase is a matrix metalloproteinase (MMP), a MMP-like enzyme, and/or a serine proteinase.

6. The composition of claim 1 wherein the degradation is associated with tissue invasion and metastasis by malignant cells, bone resorption, cartilage destruction, or destruction of soft tissues.

7. The composition of claim 1 wherein the tetracycline and the bisphosphonate are present in synergistic amounts for inhibiting the production and activity of mammalian proteinases.

8. The composition of claim 1 wherein the tetracycline is CMT-1, CMT-3, CMT-8, doxycycline, minocycline, lymecycline or combinations thereof, and the bisphosphonate compound is alendronate, clodronate (clodrinate), etidronate, medronate, nedrinate, pamidronate, tiludronate, zolendronate or combinations thereof.

* * * * *